United States Patent
Vellekoop et al.

(10) Patent No.: US 6,796,174 B1
(45) Date of Patent: Sep. 28, 2004

(54) APPARATUS FOR MEASURING A SMALL QUANTITY OF A LIQUID

(75) Inventors: Michael Johannes Vellekoop, Noordwijkerhout (NL); Kari Tapani Hjelt, Helsinki (FI); Gerrit Wignand Lubking, deceased, late of Schipluiden (NL); by Gerrit Yho Warries, executor, Utrecht (NL)

(73) Assignee: Technische Universiteit Delft, Delft (NL)

( * ) Notice: Subject to any disclaimer, the term of this patent is extended or adjusted under 35 U.S.C. 154(b) by 0 days.

(21) Appl. No.: 09/980,462

(22) PCT Filed: May 30, 2000

(86) PCT No.: PCT/NL00/00371

§ 371 (c)(1), (2), (4) Date: Jul. 19, 2002

(87) PCT Pub. No.: WO00/73746

PCT Pub. Date: Dec. 7, 2000

(30) Foreign Application Priority Data

May 31, 1999 (NL) ............................................ 1012197

(51) Int. Cl.[7] ............................................... G01F 23/26
(52) U.S. Cl. ................................................... 73/304 R
(58) Field of Search ............................ 73/304 R, 199, 73/704 R; 340/60

(56) References Cited

U.S. PATENT DOCUMENTS

| | | | | |
|---|---|---|---|---|
| 3,812,422 A | * | 5/1974 | De Carolis | ................. 324/642 |
| 4,010,650 A | * | 3/1977 | Piatkowski, Jr. | .......... 73/304 C |
| 4,646,569 A | * | 3/1987 | Cosser | .................... 73/304 R |
| 5,092,171 A | * | 3/1992 | Wallrafen | ................ 73/514.08 |
| 5,863,708 A | | 1/1999 | Zanzucchi et al. | |

FOREIGN PATENT DOCUMENTS

| | | |
|---|---|---|
| DE | 196 46 505 A1 | 5/1998 |
| EP | 0 819 942 A2 | 1/1998 |
| WO | WO96/24030 | 8/1996 |
| WO | WO98/03841 | 1/1998 |

* cited by examiner

*Primary Examiner*—J Hezron Williams
*Assistant Examiner*—John Fitzgerald
(74) *Attorney, Agent, or Firm*—Jeffrey D. Myers; Peacock, Myers & Adams, P.C.

(57) ABSTRACT

An apparatus for measuring a small quantity of a liquid, for example, in connection with a medical diagnostic test, comprising at last one chamber for receiving the liquid, which chamber comprises a bottom and upright side walls and at least two electrodes to connect to a voltage source and a measuring system for determining the electrical impedance between the electrodes. The electrodes are substantially incorporated in the bottom of the chamber, allowing the electrical impedance of the liquid itself to be determined.

13 Claims, 1 Drawing Sheet

APPARATUS FOR MEASURING A SMALL QUANTITY OF A LIQUID

CROSS-REFERENCE TO RELATED APPLICATIONS

This application is a national entry application of International Patent Application Serial No. PCT/NL00/00371, entitled "Apparatus for Measuring a Small Quantity of a Liquid" to Michael Johannes Vellekoop et al., having an international filing date of May 30, 2000, and claiming priority to Netherlands Patent Application Serial No. 1012197, having a filing date of May 30, 1999, and the specifications thereof are incorporated herein by reference.

STATEMENT REGARDING FEDERALLY SPONSORED RESEARCH OR DEVELOPMENT (Not Applicable)

INCORPORATION BY REFERENCE OF MATERIAL SUBMITTED ON A COMPACT DISK OR MICROFICHE APPENDIX (Not Applicable)

BACKGROUND OF THE INVENTION

1. Field of the Invention

The invention relates to an apparatus for measuring a volume of a quantity of a liquid, for example, in connection with a medical diagnostic test, comprising at least one chamber for receiving the liquid, which chamber comprises a bottom and upright side walls and at least two electrodes to connect to a voltage source and to a measuring system for determining the electrical impedance between the electrodes.

2. Description of Related Art

Such an apparatus is known from the international patent application WO96/24030 (PCT/US96/00911). The prior art apparatus possesses a chamber with side walls provided with electrodes. The drawback of this known apparatus, which is used, for example, for performing medical diagnostic tests on blood or the like is that the chamber for receiving the liquid has a rather large volume. This is a disadvantage since as a consequence such an apparatus, which is not only used for medical diagnostic purposes but is also applied in fine-chemical and pharmaceutical test arrays, uses large amounts of liquid. Such liquids as, for instance biochemical receptors, are costly, as a result of which it has long been endeavoured to make the type of apparatus described in the preamble smaller, especially in respect of the chamber volume. Such smaller volumes have the additional advantage of speeding up reaction rates of the liquids introduced into the apparatus, due to the reduced diffusion distances and the physical limitations inherent to a smaller chamber volume. Accordingly, the importance of precisely measuring the amount of liquid increases, as with (very) small test volumes small deviations will easily lead to inaccurate test results. With the miniaturization of the chamber that is part of such an apparatus, the problem arises that it is difficult to incorporate the electrodes into the side walls of the chamber. Moreover, a precise measurement of the volume is then no longer possible.

It is the object of the invention therefore to provide an apparatus of the kind mentioned in the preamble, that can be miniaturized to a significant extent, that makes it possible to precisely measure the liquid volume in the chamber, that can be fabricated at low costs, and that is suitable for use in automized test procedures.

BRIEF SUMMARY OF THE INVENTION

To this end the apparatus according to the invention is characterized in that the electrodes are substantially incorporated in the bottom of the chamber, allowing the electrical impedance of the liquid itself to be determined.

Surprisingly it has been shown, that by using the apparatus according to the invention it is possible to perform very precise volume measurements of the liquid in the chamber, while even the presence of a concave or convex meniscus on the liquid hardly has any negative effect on the accuracy of the measurement. Applicant believes to be able to explain this through the measurement being based on a totally different principle compared with the method of measurement using the apparatus disclosed in WO 96/24030, although the two appear to bear some relationship to one another. In the prior art apparatus, the volume is measured indirectly due to the electrical transfer between the electrode plates being influenced by the level of liquid between them, but also by the degree of electrical coupling of the electrodes to the liquid. However, in the invention an impedance measurement of the liquid itself takes place, and the degree of electrical coupling of the electrodes to the liquid is invariant with regard to the amount of liquid present in the chamber.

It is observed that from WO 98/03841 (PCT/US97/12866) a capacitive water level gauge is known wherein two electrodes are incorporated in the bottom. However, this publication is not concerned with measuring a water volume, nor is it possible to use the apparatus disclosed in this publication for a medical diagnostic test, in which it is important to be able to measure a small amount of liquid.

A first advantageous embodiment of the apparatus according to the invention is characterized in that the bottom of the chamber is substantially formed by a glass substrate. This affords the advantage that no steps need to be taken to electrically insulate the electrodes with respect to the substrate. Preferably the electrodes are then provided on the glass substrate, and are embedded in an insulation layer provided on the glass substrate.

A second advantageous embodiment of the apparatus according to the invention is characterized in that the bottom of the chamber is substantially formed by a silicon wafer. On this basis the apparatus can be fabricated at low costs, the chamber of the apparatus can be given a precise volume, while the same can be conveniently embodied by applying the appropriate semiconductor technology for direct coupling with an automatic, possibly computerized, measuring system.

Desirably in this embodiment, the silicon wafer is provided with a first insulation layer, preferably of $SiO_2$. This electrically insulates the electrodes with respect to the wafer, and further reduces the undesirable capacitive coupling of the electrodes to the silicon wafer.

It is further desirable for the electrodes to be provided on the first insulation layer of the silicon wafer and for them to be embedded in a second insulation layer, preferably $Si_xN_y$, which is provided on the first insulation layer. In this way the electrodes are prevented from being galvanically coupled with the liquid to be introduced into the chamber.

It is further advantageous that the upright side walls are formed by etching insulation material provided on the second insulation layer. Production-technically this can be realized quite easily.

The invention provides an apparatus which, in a preferred variant, is characterized in that the chamber is equipped to receive liquid up to an amount of maximally 2 nanolitres.

In addition the invention has the advantage that in a desirable embodiment it can be fabricated such that it comprises a plurality of chambers arranged in an array. This is very convenient for performing extensive testing procedures.

The invention is further embodied in a method for measuring a quantity of liquid using the apparatus according to the invention, and is characterized in that the voltage source is an alternating voltage source having a frequency of at least approximately 15 kHz. The advantage of this measure is that the effect of the coupling capacity between the electrodes and the liquid is negligible, which contributes to the precision in measuring the quantity of liquid introduced into the chamber.

BRIEF DESCRIPTION OF THE SEVERAL VIEWS OF THE DRAWINGS

The invention will now be further explained with reference to the drawing, which in FIG. 1, shows a schematic cross section of a first embodiment of the apparatus according to the invention; and in FIG. 2, shows a schematic cross section of a second embodiment of the apparatus according to the invention.

Identical reference numbers used in the Figures refer to similar parts.

DETAILED DESCRIPTION OF THE INVENTION

Figure 1:
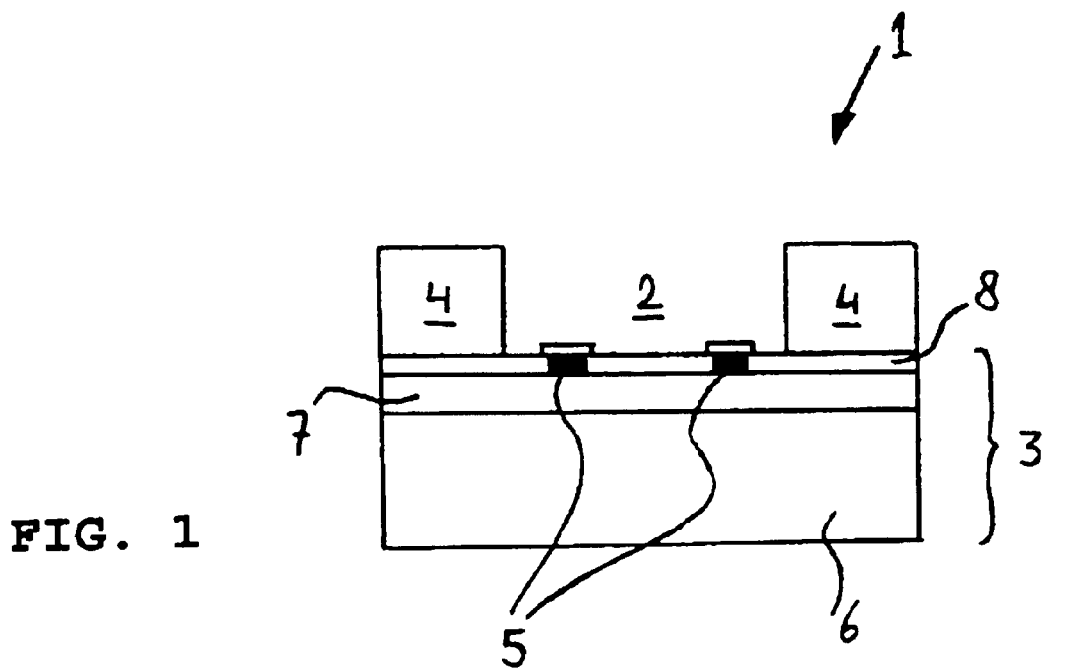
Figure 2:
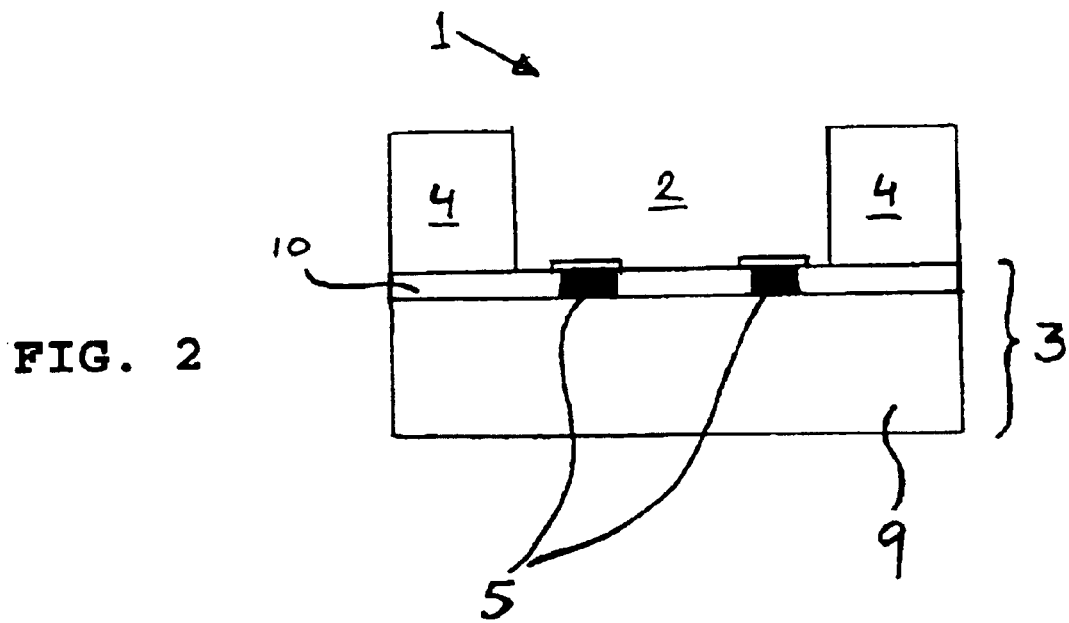

In the FIGS. 1 and 2 the apparatus is generally indicated with reference number 1. Liquid whose volume is to be measured may be introduced into the chamber 2 of the apparatus. This chamber 2 comprises a bottom 3 and upright side walls 4. Further, electrodes 5 are provided which are incorporated in the bottom 3 of the chamber 2. Via electric cables (not shown), the electrodes 5 can be connected to a voltage source and a measuring system in a manner with which the person skilled in the art is fully acquainted, which electrodes serve to determine the electrical impedance between the electrodes 5 as it is being formed by the liquid to be introduced into the chamber 2.

A first embodiment of the apparatus according to the invention will now be elucidated with reference to FIG. 1. The bottom 3 of the chamber 2 is substantially formed by a silicon wafer 6. The silicon wafer 6 is provided with a first insulation layer 7, which is preferably $SiO_2$. The electrodes 5 are provided on the first insulation layer 7 of the silicon wafer 6, and embedded in a second insulation layer 8, preferably $Si_xN_y$, which is provided on the first insulation layer 7. The upright side walls 4 finally are preferably formed by etching insulation material applied to the second insulation layer a. For this purpose it is convenient to use, for example, $SiO_2$.

FIG. 2, shows a second embodiment of the apparatus according to the invention. In this embodiment the main portion of the bottom 3 is formed by a glass substrate 9. The electrodes 5 are provided on the glass substrate 9, being embedded in an insulation layer 10. Again, any suitable material may be used for the insulation layer 10 such as, for example, $Si_xN_y$. In this second embodiment finally, the upright walls 4 are also preferably formed by etching the insulation material applied to the insulation layer 10.

Although for the sake of clarity the invention is explained in an embodiment comprising only one chamber 2, it should be appreciated that the apparatus according to the invention may also be embodied comprising a plurality of adjacently arrayed chambers 2, which appropriately may, for example, have the following dimensions. The dimensions of the array may be 5 by 5 $mm^2$, possibly comprising eight by twelve (=96) chambers 2, having a width, length and height of 200 $\mu$m, 200 $\mu$m, and 6–40 $\mu$m, respectively. The liquid volume that such a chamber 2 can contain is approximately 0.2–1.5 nanolitres. The first insulation layer 7 of the apparatus 1 then has, for example, a thickness of 2 $\mu$m. The electrodes 5 may be of aluminium, of a thickness of 300 nanometres, and covered with a 500-nanometres-thick $Si_xN_y$ layer.

The preceding discussion and dimensional examples should be understood as being non-limitative exemplary embodiments. The protective scope of the invention is determined exclusively by the appended claims. The preceding discussion merely serves to elucidate said claims.

What is claimed is:

1. An apparatus for measuring a volume of a quantity of a liquid, comprising at least one chamber for receiving the liquid, which chamber comprises a bottom and upright side walls end at least two electrodes to connect to a voltage source and to a measuring system for determining an electrical impedance between the electrodes, wherein the electrodes are disposed and incorporated only in the bottom of the chamber, allowing the electrical impedance of the liquid itself to be determined.

2. An apparatus according to claim 1, wherein the volume of said at least one chamber is maximally 2 nanolitres.

3. An apparatus according to claim 1, wherein said apparatus comprises a plurality of chambers arranged in an array.

4. An apparatus according to claim 1, wherein said apparatus is connected to an alternating voltage source having a frequency of at least approximately 15 kHz.

5. An apparatus according to claim 1, wherein the bottom of the chamber is substantially formed by a glass substrate.

6. An apparatus according to claim 5, wherein the electrodes are provided on the glass substrate, and are embedded in an Insulation layer provided on the glass substrate.

7. An apparatus according to claim 6, wherein the upright side walls are formed by etching insulation material provided on the insulation layer.

8. An apparatus according to claim 1, wherein the bottom of the chamber Is substantially formed by a silicon wafer.

9. An apparatus according to claim 8, wherein the silicon wafer is provided with a first insulation layer.

10. An apparatus according to claim 9, wherein the electrodes are provided on the first insulation layer of the silicon wafer and are embedded in a second insulation layer, which is provided on the first insulation layer.

11. An apparatus according to claim 9, wherein said first insulation layer comprises $SiO_2$.

12. An apparatus according to claim 10, wherein the upright side walls are formed by etching insulation material provided on the second insulation layer.

13. An apparatus according to claim 10, wherein said second Insulation layer comprises $Si_xN_y$.

* * * * *